United States Patent
Vicatos

(10) Patent No.: US 9,452,054 B2
(45) Date of Patent: Sep. 27, 2016

(54) ROTATING HINGE KNEE PROSTHESIS

(71) Applicant: UNIVERSITY OF CAPE TOWN, Cape Town (ZA)

(72) Inventor: George Vicatos, Cape Town (ZA)

(73) Assignee: UNIVERSITY OF CAPE TOWN, Cape Town (ZA)

( * ) Notice: Subject to any disclaimer, the term of this patent is extended or adjusted under 35 U.S.C. 154(b) by 0 days.

(21) Appl. No.: 14/383,338

(22) PCT Filed: Mar. 5, 2013

(86) PCT No.: PCT/IB2013/051728
§ 371 (c)(1),
(2) Date: Sep. 5, 2014

(87) PCT Pub. No.: WO2013/132425
PCT Pub. Date: Sep. 12, 2013

(65) Prior Publication Data
US 2015/0045899 A1    Feb. 12, 2015

(30) Foreign Application Priority Data

Mar. 6, 2012  (ZA) .................................. 2012/01641

(51) Int. Cl.
*A61F 2/38* (2006.01)
*A61F 2/30* (2006.01)

(52) U.S. Cl.
CPC .............. *A61F 2/3845* (2013.01); *A61F 2/385* (2013.01); *A61F 2/3854* (2013.01); *A61F 2002/30387* (2013.01); *A61F 2250/0073* (2013.01)

(58) Field of Classification Search
CPC ...... A61F 2/38; A61F 2/3836; A61F 2/3854; A61F 2/3859; A61F 2/3868
See application file for complete search history.

(56) References Cited

U.S. PATENT DOCUMENTS 3,824,630 A    7/1974  Johnston
4,309,778 A *  1/1982  Buechel ................ A61F 2/3868
                                                    623/20.29

(Continued)

FOREIGN PATENT DOCUMENTS

DE    30 22 668 A1    12/1981
DE    41 02 509 A1    7/1992

(Continued)

OTHER PUBLICATIONS

International Search Report issued in PCT/IB2013/051728 mailed on Jun. 13, 2013 (3 pages).

(Continued)

*Primary Examiner* — Yashita Sharma
*Assistant Examiner* — Daniel Bissing
(74) *Attorney, Agent, or Firm* — Osha Liang LLP

(57) ABSTRACT

A knee prosthesis is provided having a femoral component (1) with a pair of laterally spaced condylar formations (2) at one end, and a tibial component (3) having a transverse platform (4) supporting a shock absorbing bumper (5) interposed between the platform and condylar formations with the tibial component supporting a ball (6) of a ball and socket joint. The socket (8) is provided in a generally cylindrical bearing (9) having an axis extending generally parallel to a longitudinal axis of the femoral component. The bearing is held captive in a recess that is between the two laterally spaced condylar formations and is formed in the region of said end of the femoral component. The axis of the bearing is preferably inclined laterally at an angle of about 5° relative to the axis of the femoral component so that it is able to line up with a mechanical axis of a lower limb.

10 Claims, 4 Drawing Sheets

(56) References Cited

U.S. PATENT DOCUMENTS

| | | | |
|---|---|---|---|
| 5,824,102 A | 10/1998 | Buscayret | |
| 2006/0030945 A1* | 2/2006 | Wright | A61F 2/30721 623/20.15 |
| 2007/0050039 A1* | 3/2007 | Dietz | A61F 2/3609 623/19.13 |
| 2012/0310362 A1* | 12/2012 | Li | A61F 2/38 623/20.32 |
| 2012/0323333 A1* | 12/2012 | Metzger | A61F 2/389 623/20.32 |

FOREIGN PATENT DOCUMENTS

| | | | | |
|---|---|---|---|---|
| DE | 4102509 A1 | * | 7/1992 | ............. A61F 2/385 |
| GB | 487177 | * | 6/1936 | |

OTHER PUBLICATIONS

Written Opinion of the International Searching Authority issued in PCT/IB2013/051728 mailed on Jun. 13, 2013 (5 pages).

\* cited by examiner

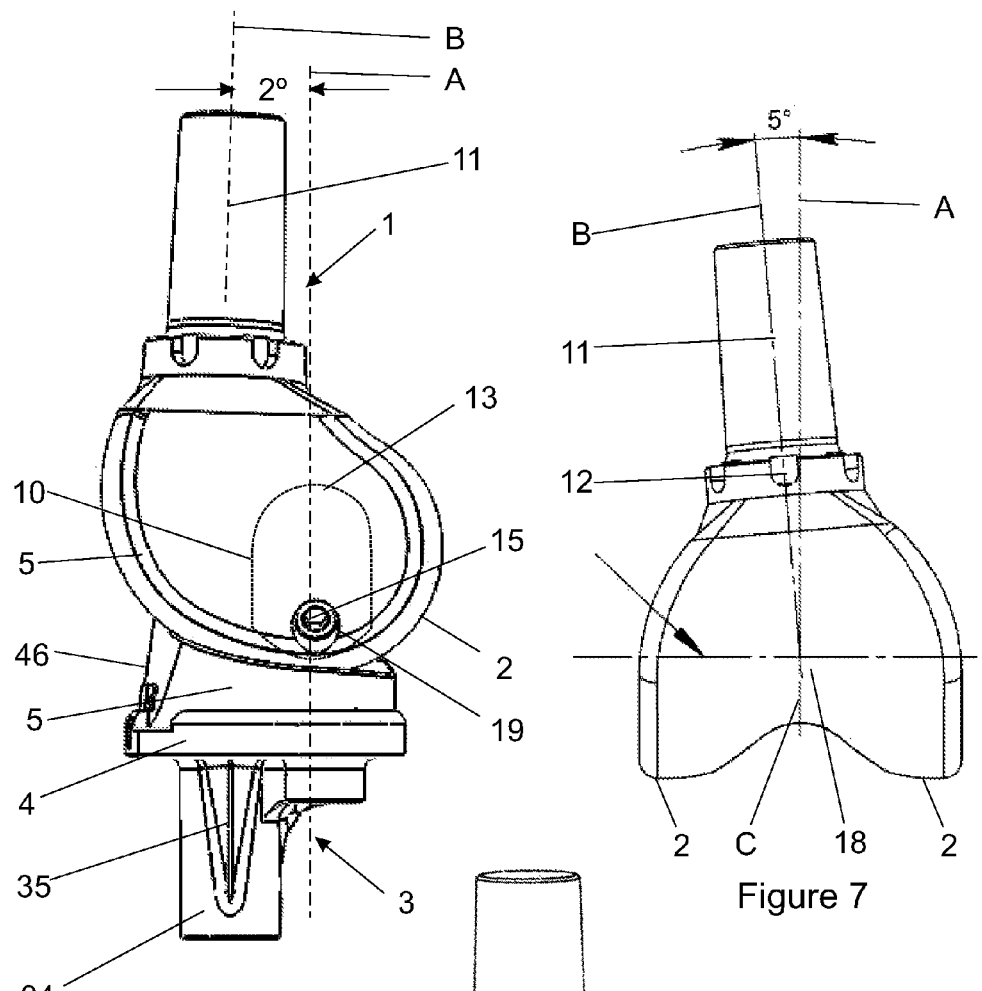
Figure 5
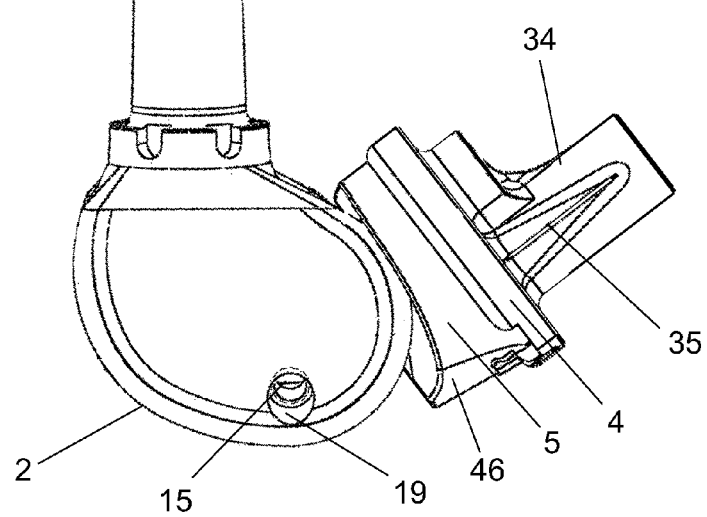
Figure 7
Figure 6

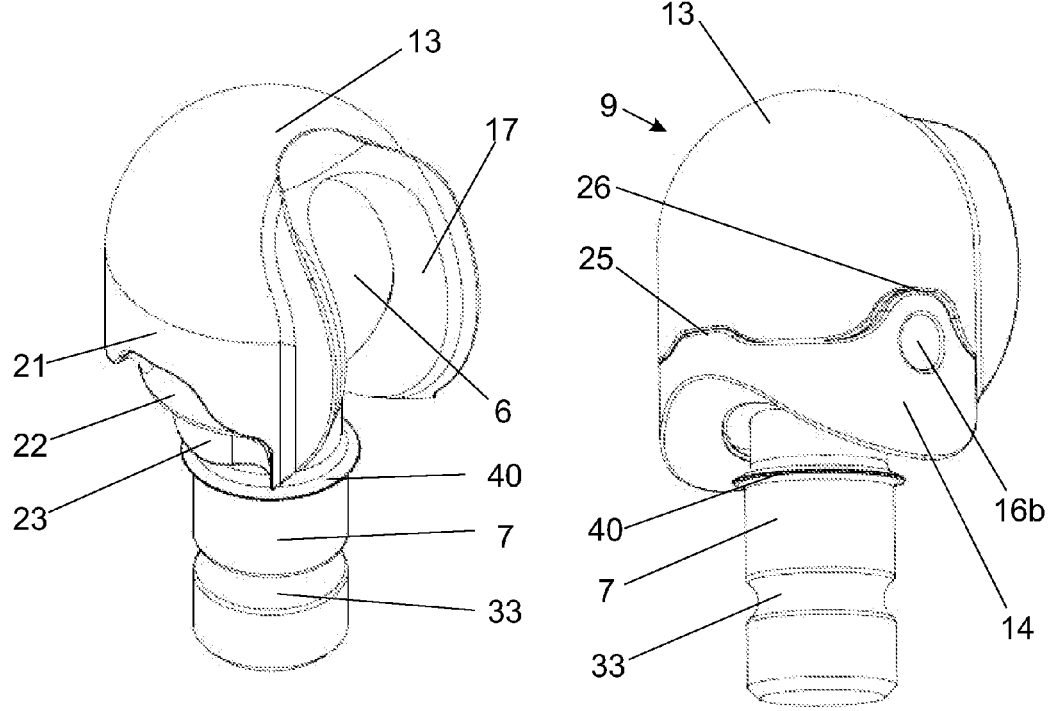
Figure 8
Figure 10
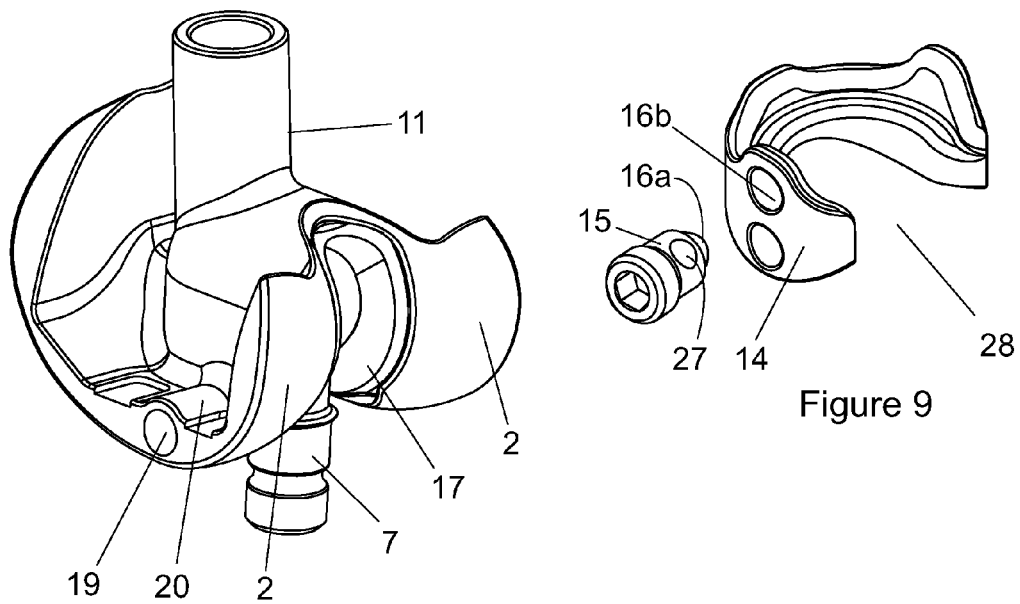
Figure 11
Figure 9

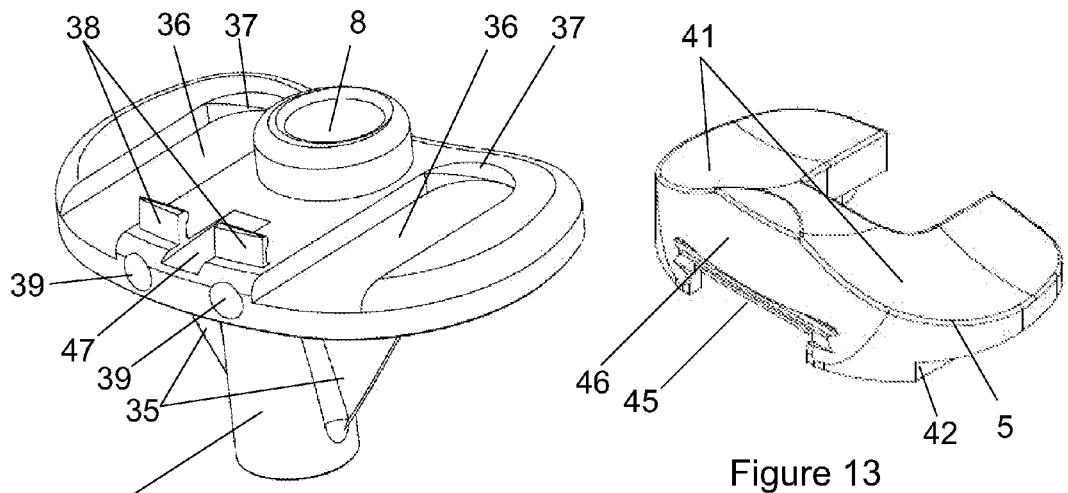
Figure 12
Figure 13
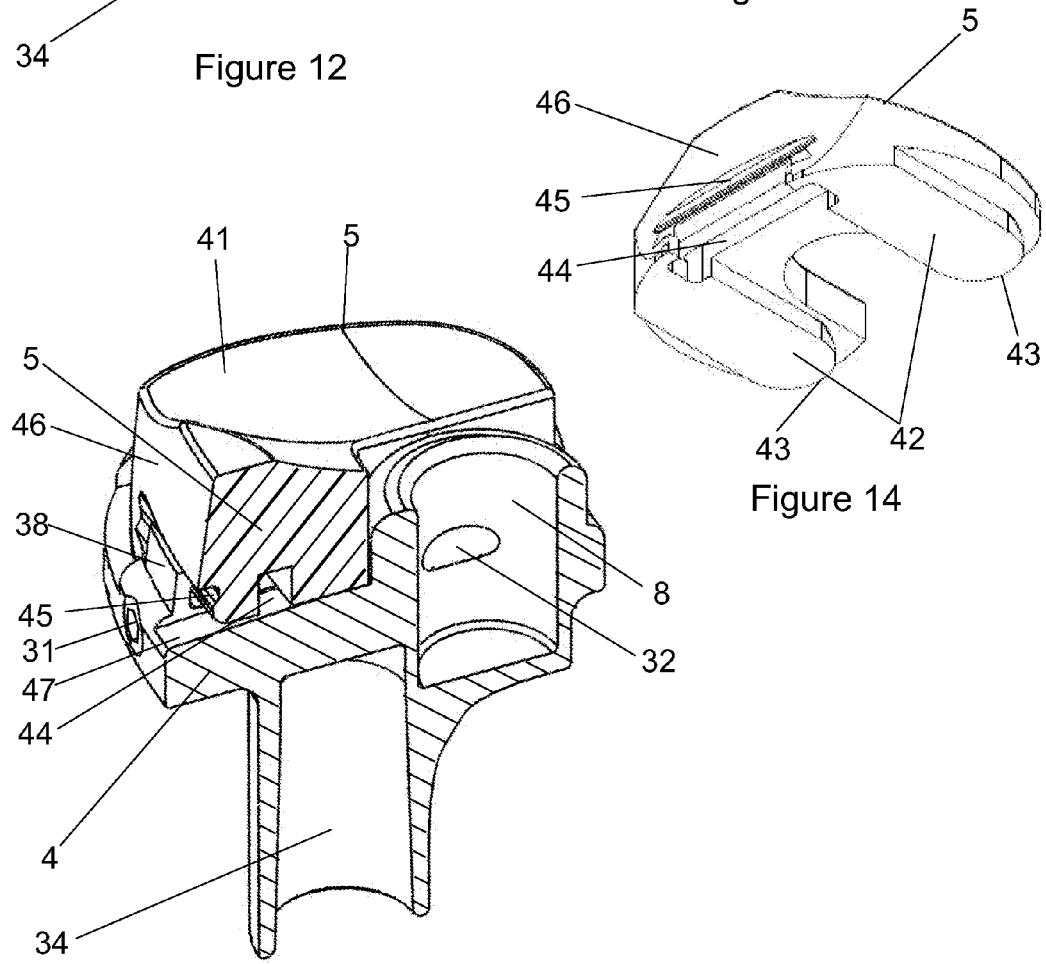
Figure 14
Figure 15

ROTATING HINGE KNEE PROSTHESIS

CROSS-REFERENCE TO RELATED APPLICATIONS

This application is a National Stage application of International Patent Application No. PCT/IB2013/051728, filed on Mar. 5, 2013, which claims priority to South African Patent Application No. 2012/01641, filed on Mar. 6, 2012. Both priority applications are hereby incorporated by reference in their entirety.

FIELD OF THE INVENTION

This invention relates to a rotating hinge knee prosthesis that is used to surgically replace a damaged or non-functional knee joint in patients in need of such replacement. The knee prosthesis is of the type comprising a femoral component for surgical attachment directly or indirectly to the femur of a patient and a tibial component that is to be surgically attached, directly or indirectly, to the tibia. The knee prosthesis is of the type that may be considered to be of the rotating hinge type.

BACKGROUND TO THE INVENTION

Knee prostheses have been produced in numerous different types, the vast majority of which have distinct generally vertical and generally horizontal hinge axes. Such an arrangement of hinges does not provide for a realistic hinging movement between the femur and tibia and therefore does not sufficiently accurately replicate the function of a natural biological knee.

In an apparent attempt to overcome this shortcoming of most knee prostheses, the company MUTARS has made available a knee prosthesis in which a femoral component and a tibial component are attached by way of a ball and socket joint. The socket is formed in a generally cylindrical plastic element that is received in a transverse complementary passage passing generally horizontally through the shaped end of a femoral component. The axis of the generally cylindrical plastic element and that of a stem supporting the ball are therefore at right angles to each other.

The ball and socket formations do indeed provide for a more realistic hinging movement between the femur and tibia. However, the structural configuration of the plastic element and femoral component whereby the socket is provided has some serious drawbacks in the event that the prosthesis needs to be maintained or a component thereof needs to be replaced or serviced in some way. In such an event extensive surgery is required and, in fact, the surgery necessary is substantially as extensive as the original implant surgery.

An improved ball and socket formation is also presented by MUTARS, where the socket is a metallic cylindrical component inserted and locked in-between the intracondylar space of the femoral condyles and a half-spherical metal bearing which is attached to the tibila implant. However, metal-on-metal articulation is not desirable in implants of this nature. Design specifications of this configuration allows flexion, extension and rotation of the knee, but again replacement of worn parts requires complete dismantling of the prosthesis and major time-consuming surgery.

There is a need therefore for a knee prosthesis that is better configured for maintenance or repair purposes.

SUMMARY OF THE INVENTION

In accordance with this invention there is provided a knee prosthesis comprising a femoral component having at one end a pair of laterally spaced condylar formations, and a tibial component having a transverse platform supporting a shock absorbing bumper interposed between the platform and condylar formations with the tibial component supporting a ball of a ball and socket joint whereof the socket is held captive by the femoral component, the knee prosthesis being characterised in that the socket is provided in a generally cylindrical bearing having an axis extending generally parallel to a longitudinal axis of the femoral component with the bearing being held captive in a recess that is between the two laterally spaced condylar formations and is formed in the region of said end of the femoral component.

Further features of the invention provide for the axis of the bearing to be inclined laterally relative to the axis of the femoral component, typically at an angle of about 5° so that it is able to line up with a mechanical axis of the lower limb; for the bearing to be held captive in the recess in the femoral component by means of at least two oppositely and inwardly directed fasteners, that may have their axes inclined somewhat upwards towards the socket of the bearing and preferably having semi-spherical inner ends cooperating with complementarily shaped recesses associated with the bearing; for screw-threaded passages in tubular formations that are integral with the femoral component to receive the screw threaded fasteners; for the bearing to have a domed inner end and a short circular cylindrical part extending from the domed inner end; for the bearing to be made of a suitable polymeric material, especially a suitable mechanically and chemically resistant, especially wear resistant, polymeric material such as a polyether ether ketone (PEEK); for the fasteners to cooperate with a suitably rigid bearing support collar that engages the bearing to hold it captive in its position in the recess in the femoral component; and for the bearing to have a slot cooperating with a stem carrying the ball of the ball and socket joint to provide for bending of the prosthesis in use, corresponding to the angles of flexing of the prosthetic knee of from 0° to about 130°.

Still further features of the invention provide for the ball of the ball and socket to be carried by a stem fitted into a cylindrical socket provided in the platform of the tibial component with the stem being held captive in the cylindrical socket by means of an offset transverse fastener having a smooth cylindrical section cooperating tangentially with a circumferential groove in the outer surface of the stem; for the tibial component to have a tapered socket for receiving a tibial intramedullary stem in taper lock cooperation with each other; and for medial and lateral fins to stabilise the platform relative to the tapered socket.

It is a particular feature of the invention that the bumper have shaped surfaces cooperating with the condylar surfaces of the femoral component with the bumper being attached to the platform of the tibial component by means of inter-engaging dovetail formations at one end of a pair of parallel laterally spaced shoe formations on the under surface of the bumper and a pair of oppositely directed catches formed integral with the platform.

The femoral component is, at the present state of materials development, preferably made of a titanium alloy such as $TiAl_6V_4$ with highly polished articulating condylar surfaces being thermally treated to convert them to a ceramic surface. The tibial component is, at the present state of materials development, preferably made of the same titanium alloy without any thermal treatment of any surface. The ball and stem, on the other hand, are currently preferably made of a cobalt chrome molybdenum alloy CoCrMo.

The bumper is preferably made of a suitably impact damping plastics material such as an ultrahigh density polyethylene material (UHMWP).

It is to be noted that fitment of the socket to the ball may be achieved by causing the socket to flex so that the ball is snap fitted into the socket. Such an action may not be appropriate in the case of some polymeric materials of which the bearing may be made and this is especially so in the case of at least some polyether ether ketone materials that would otherwise be suitable for the purpose that may shatter if distorted to any appreciable extent. In such an instance it is envisaged that the polymeric part of the bearing can be moulded in situ onto the ball thereby avoiding any such difficulties.

In order that the above and other features of the invention may be more fully understood one embodiment thereof will now be described with reference to the accompanying drawings.

BRIEF DESCRIPTION OF THE DRAWINGS

In the drawings:

FIG. 5 is a side view of the knee prosthesis with the femoral and tibial components in alignment corresponding to a straightened leg;

FIG. 6 is the same as FIG. 5 but showing the tibial component fully rotated to a bent condition;

FIG. 7 is a front view of the femoral component showing especially the condylar formations;

FIG. 8 is a perspective view somewhat from the posterior or rear of a bearing showing the ball and stem in situ therein but with the support collar absent;

FIG. 9 illustrates in perspective view the support collar and one of its locking fasteners on their own;

FIG. 10 is a perspective view of the bearing and ball and stem assembly from a somewhat anterior or frontal direction;

FIG. 11 is a perspective view of a kind of femoral component different to those illustrated in FIGS. 1-7, used in specific femoral condyles resurfacing and proximal tibia replacement operations with the ball and stem in situ;

FIG. 12 is a perspective view of the tibial component without the bumper or ball and stem in situ;

FIG. 13 is a front perspective view of the bumper of the knee prosthesis taken from somewhat above;

FIG. 14 is a front perspective view of the bumper taken from somewhat below; and, FIG. 15 is a partly sectioned view of the assembly of the tibial component and bumper and showing the attachment means for the stem of the ball with the stem and the ball removed.

DETAILED DESCRIPTION WITH REFERENCE TO THE DRAWINGS

Figure 1:
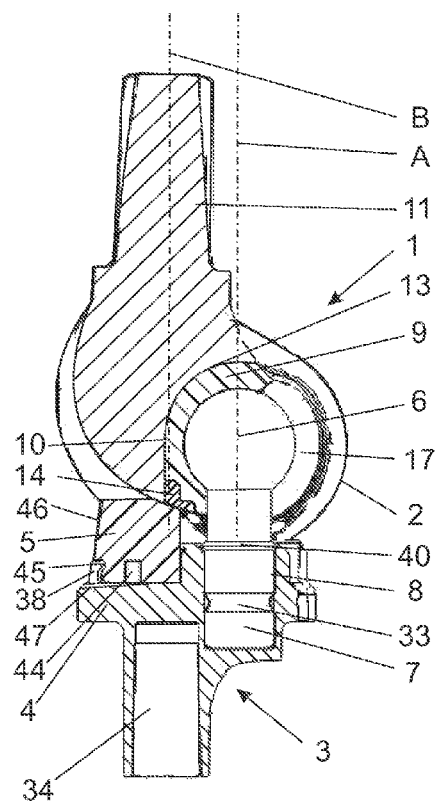
FIG. 1 is schematic side section of one embodiment of knee prosthesis according to the invention.

In the embodiment of the invention illustrated in the drawings, a knee prosthesis comprises a femoral component (1) having at one end a pair of laterally spaced condylar formations (2), and a tibial component (3) having a transverse platform (4) supporting an impact absorbing bumper (5) interposed between the platform and condylar formations.

The femoral component and tibial component are attached together by way of a ball and socket joint whereof the ball (6) is carried at the upper end of a supporting stem (7) that is held captive in a socket (8) in the platform of the tibial component whilst a co-operating socket of a ball and socket joint is formed within a bearing (9) that is held captive in a recess (10) relative to the femoral component.

The femoral component has an anatomical shape with the design taking into account a large number of scaled x-ray films. It may have a range of sizes such as large, medium and small sizes for each of the left and right sides. The centre of flexion is in line with the natural medial and lateral condylar formations.

The femoral component of the prosthetic knee has a tapered stem (11) which allows the prosthetic knee to "taper-lock" and assemble with cylindrical extensions (having complementarily tapered counterparts), making it possible to achieve a variety of femoral bone resection lengths. At the base of the stem are six notches (12) that allow the extensions to lock at certain positions (60° angular intervals) and thereby provide rotational stability. The notches also provide orientation should the knee be linked with femoral components that require a definite orientation such as proximal femoral implants.

As provided by this invention, the bearing has an outer generally cylindrical shape with a domed inner end (13) that is received in the recess (10) formed in the femoral component approximately centrally between the condylar formations and that is complementarily shaped to the outer surface of the bearing. The axis (A) of the bearing and recess is generally parallel to a longitudinal axis (B) of the femoral component but is angularly offset laterally so as to be capable of being in line with the mechanical axis of the lower limb that is indicated by the letter (C) in FIG. 7.

In this embodiment of the invention the bearing itself is made of a moulded plastic material having appropriate wear and chemical resistance and it is especially favoured to utilise a polymeric material such as a polyether ether ketone (PEEK). It is noted that at least some polyether ether ketones are semi-crystalline thermoplastic materials with excellent mechanical and chemical resistance properties. As indicated above, it is believed to be possible that, in the event of the polymeric material being fragile or brittle and therefore susceptible to damage should it be clipped on to the ball of the ball and socket joint, the bearing could be moulded directly over the ball using a suitable mould.

Figure 4:
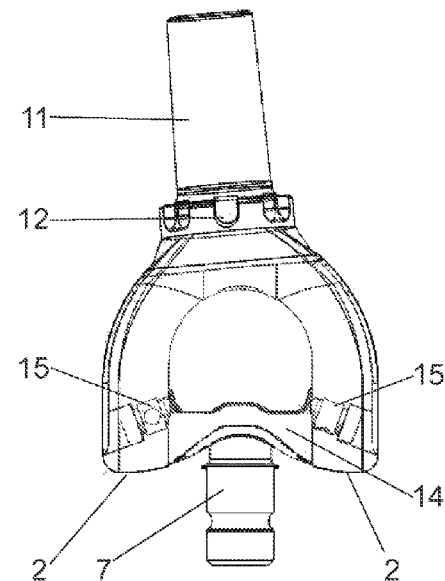
FIG. 4 is an anterior or front transparent view of the femoral component with the bearing, ball and stem present.

The lower edge of the bearing is shaped for effective cooperation with a rigid collar (14) whereby the bearing is held captive in the recess. The collar (14) as seen in FIG. 1, FIG. 4, and FIG. 9 is maintained in the installed condition by means of two diametrically opposite and inwardly directed screw-threaded fasteners (15) that may have their axes inclined somewhat upwards towards the socket of the bearing. The fasteners have semi-spherical inner ends (16a) cooperating with complementarily shaped recesses (16b) provided at diametrically opposite positions in the outer surface of the collar (14) (see FIG. 9).

FIG. 9 is actually a perspective view of a large size support collar (14) that has two alternative part spherical shaped recesses (16b) that can be selectively used to support the bearing inside the large size femoral condyles. In smaller sized rigid collars, such as a small or medium size, there may be only one spherical shaped recess (16b). In the instance that there are two alternative recesses, the arrangement allows the bearing locking fasteners to engage, either in the top or bottom recess, depending on the size and type of femoral condyles used. For example, the condyles that are illustrated in FIGS. 1-7 may use the top recesses and resurfacing condyles that are illustrated in FIG. 11 may use the bottom recess.

Figure 2:
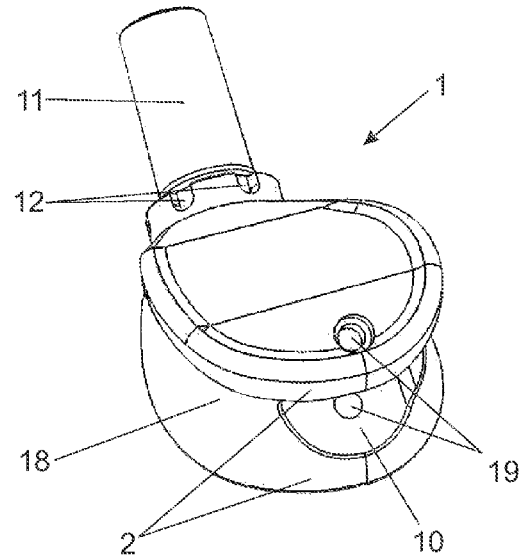
FIG. 2 is a perspective view of the femoral component taken from somewhat beneath the condylar formations.
Figure 3:
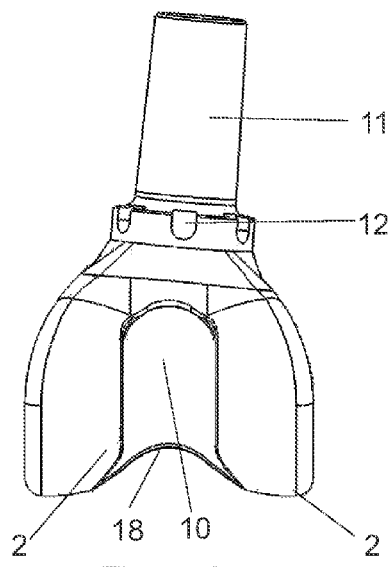
FIG. 3 is a posterior or rear view of the femoral component with the bearing, ball and stem absent.

As shown in FIG. 2, at the medial and lateral exterior surfaces of the condylar formations are two screw-holes (19) through which the two screw-threaded fasteners pass in order to engage the collar (14) to lock the bearing in position. The screw-threaded fasteners extend into complementarily screw-threaded passages in tubular formations (20) that are integral with the femoral component (see FIGS. 4 and 11 in particular). In the instance illustrated in FIG. 4, the bearing locking screw-threaded fasteners are inclined towards the bearing socket whilst in the instance illustrated in FIG. 11 the locking fasteners are placed with no inclination towards the bearing socket and are perpendicular to the axis of the bearing. The screw-threaded fasteners have friction affording inserts (27) projecting somewhat from their sides to engage the wall of the hole and form a friction lock therewith.

The bearing is formed with a longitudinally extending slot (17) that receives the stem (7) carrying the ball (6) of the ball and socket joint so that the ball and socket, when the prosthetic knee bends in use, can accommodate possible bending of the knee corresponding to the angles from 0° to about 130° about a transverse axis.

It may be that the internal and external spherical surfaces are not concentric with each other. The centre of the internal spherical surface may be distally displaced in order to have more material at the most proximal part of the dome. As shown in FIG. 8, distally the bearing has a formed exterior surface which comprises three coaxial cylinders (21, 22, 23) of different diameters, thereby making a stepped cylindrical construction. The outermost cylindar (21) has the same external diameter as the semi-spherical inner end of the bearing and has three indentations (25, 26) in its distal end edge, namely, one anteriorly (25), one laterally and one medially (26). The collar has a cylindrical external surface and a stepped cylindrical internal surface which corresponds to the external cylindrical structure (21, 22, 23) of the bearing. The bearing support collar (14) has a circumferential cut out portion (28) posteriorly corresponding to the slot (17).

Anteriorly the knee has an anatomically-shaped shallow groove (18) which allows for patellar traction. This groove continues distally and curves at a constant radius posteriorly around a fixed centre of curvature which is the "centre of the knee". The proximal tapered stem has a valgus angle of 5°, as shown in FIG. 7. It is inclined posteriorly at an angle of 2°, as shown in FIG. 5.

The surface contours of the condylar formations are designed in such way that they form medially and laterally two toroidal surfaces which blend with the anterior surface and with the patellar groove (18). Particularly, the femoral condyles illustrated in FIG. 11, are designed in such a way that the patellar grove (18) is also inclined to be in line with the anatomical axis of the femur. The femoral component is made of titanium alloy (TiAl6V4) and is thermally treated to convert highly polished articulating surfaces into ceramic material, as mentioned above.

The stem that extends into the cylindrical socket provided in the platform of the tibial component is held captive in the socket by means of an offset transverse fastener (31) having a smooth cylindrical section (32) cooperating tangentially with a circumferential groove (33) in the outer surface of the stem when it is fully located in its cylindrical socket in the platform of the tibial component.

The tibial component has a tapered socket (34) for receiving a tibial intermediary stem (not shown) in taper lock cooperation with each other. Medial and lateral fins (35) stabilise the platform relative to the tapered socket. The tibial component is made of the same titanium alloy as the femoral component without any thermal treatment of any surface whilst the ball and stem are made of a cobalt chrome molybdenum alloy CoCrMo.

The platform (4) of the tibial component supports the bumper (5) and with that end in view the surface of the platform has a pair of parallel laterally spaced channels (36) of rectangular section having overhanging formations (37) at one end. A pair of inwardly directed catches (38) is formed integral with the platform in the opposite end region of the channels and in between them in the transverse direction. Two laterally spaced holes (39), either of which can receive the transverse fastener (31), are also provided in the platform between the channels and each provides a possible hole for receiving a fastener (31) on either of two diametrically opposite sides of the stem so that the smooth cylindrical section (32) of the fastener, protruding inside the cylindrical socket, can cooperate with the groove in the stem in order to hold it captive. The degree to which the stem can enter the socket is limited by a circumferential ridge (40) encircling the stem at an appropriate position to provide the ball with its final working position. The ridge engages the entrance to the socket in the installed position. The stem identifies the vertical axis of rotation of the femoral component, while the taper socket (34) identifies the axis of the tibial shaft. The separation distance of these two axes is determined from a large number of x-rays.

The bumper is made of a suitable ultrahigh density polyethylene material and has shaped surfaces (41) for cooperating with the condylar surfaces of the femoral component. The bumper has on its opposite surface a pair of parallel laterally spaced shoe formations (42) that fit neatly into the channels formed in the platform of the tibial component and which have forwardly directed projections (43) for entering underneath the overhanging formations (37) at the ends of the channels in the manner of dovetail formations.

The bumper is further provided with a deep rectangular cross-sectioned channel (44) extending transversely across the bumper at a position spaced inwards from the edge closer to its front face (46) and opposite the ends of the shoe formations having the projections so as to provide the bumper with sufficient resilience to enable it to be forced into its installed position. In so doing, the material of the bumper deforms so that the catches (38) can be forced past the edge of the bumper and snap into engagement with a cooperating groove (45) in the adjacent face (46) of the bumper to lock it in its installed position. The bumper can be removed by forcing it off the platform using a screwdriver or other like tool that can be inserted by way of an inclined depression (47) in the face of the platform between the two channels to prise the bumper off the platform.

In operation, movement of the knee is achieved by the combined control of the femoral bearing assembly and the bumper carried by the tibial component. Since a universal bearing does not have a directional constraint, the knee would have been free to rotate in all directions. This freedom is restricted by the articulating surface on the bumper, which allows the femoral component to flex in the anterior posterior direction. The flexion angle ranges between 0° (knee extended as shown in FIG. 5) and 130° (knee fully flexed as shown in FIG. 6). The bearing is situated at the knee's centre of rotation, thus enabling the knee to flex with respect to the tibia At knee extension, the position of the femoral component is controlled by the shape of the bumper, which anteriorly and proximally is shaped to engage with the patellar groove (18). As soon as the femoral component is flexed, the bearing assembly together with the bumper allows a limited rotation of the femoral component relative to the tibial component, around the tibial axis, about 20° in total, 10° in each of the medial and lateral directions. This is achieved by the toroidal surfaces of the bumper and the femoral component which restrict rotation. Thus the knee can flex and rotate simultaneously through its full range of motion.

The bearing axis is situated posteriorly to the tapered stem (11) of the femoral component so that the forces acting on the knee during gait, maintain the knee in extension without the danger of collapsing. Also during knee extension, the anterior and distal surface of the patellar groove pivot at the anterior and proximal surface of the bumper. The forces during gait and, in particular at knee extension, will tend to pull out the bearing stem from the socket in the tibial component.

In addition to this, as the joint rotates mediolaterally at flexion, a reaction force is generated from the bumper acting on the femoral component. This force also tends to lift the stem of the bearing assembly off the tibial platform. These combined vertical forces on the bearing are counteracted by a force generated from the bearing locking screws (15), which holds the bearing assembly and consequently the femoral component in position.

The benefit of this knee and bearing is on the ergonomics; the ease of assembly and dismantling the knee joint; and also on its ability to combine with a variety of tibias and femoral components. For example, a solid distal femoral component can combine with the resurfacing tibial component or it can combine with a proximal tibial component thus replacing the entire compartment of the knee joint. Various combinations of different sizes of components are also possible.

The design of the femoral component accommodates surgical replacement of the natural distal femur. A deviation of this design is to resurface/replace the natural condyles with a resurfacing femoral component.

This type of femoral component maintains the bearing and its locking system in both the femoral and tibial parts of the knee joint. However, it incorporates empty spaces medially and laterally as illustrated in FIG. 11.

The resurfacing femoral component has special features which facilitate the fitting of the resurfacing femoral component distally onto the femur.

Special jigs may be employed for assisting with the resurfacing and shaping of the natural condyles and may be an integral part of the instruments supporting this kind of surgery.

It should be noted that the bearing housing has spherical and cylindrical surfaces in order to reduce the stress risers in the femur. Its dimensions are such that mediolaterally and anterioposteriorly it requires minimum bone removal at the intercondylar space of the femur. It has an intramedullary stem receptor which is inclined at 5° valgus angle. The patellar grove is also inclined at 5° valgus angle while the lateral condyle is raised to form an anterior lateral ridge, in order to assist with the smooth transmission of forces acting on the patella, during gait. The receptor is tapered internally in order to facilitate a "taper-lock" anchorage with the intramedullary stem.

The resurfacing femoral component can combine with either of the two types of tibias, i.e. the resurfacing type as shown in FIG. 12 and the proximal tibia type (not shown), making available four main combinations of joint replacements. Each combination has its own subdivisions depending on the size of the knee required, thus providing the surgeon with a large variety of options to decide and choose the best option for a particular patient.

It will be understood that numerous variations may be made to the embodiment of the invention described above without departing from the scope hereof.

The invention claimed is:

1. A knee prosthesis comprising:
   a femoral component having at one end a pair of laterally spaced condylar formations; and
   a tibial component having a transverse platform supporting a shock absorbing bumper interposed between the platform and condylar formations with the tibial component supporting a ball of a ball and socket joint, the ball fixed in its axial position relative to the tibial component, and whereof the socket is held captive by the femoral component,
   wherein the socket is provided in a generally cylindrical bearing having an axis extending generally parallel to a longitudinal axis of the femoral component with the bearing being held captive in a recess that is between the two laterally spaced condylar formations and is formed in the region of said end of the femoral component, and
   wherein a suitably rigid bearing support collar engages the bearing to hold it captive in its position in the recess in the femoral component and the hearing is held captive in the recess by at least two oppositely and inwardly directed screw threaded fasteners received in screw-threaded passages in tubular formations that are integral with the femoral component with the screw threaded fasteners engaging the bearing support collar such that, in operation, movement of a knee is achieved by the combined control of the femoral bearing assembly and the bumper carried by the tibial component with freedom of movement of the knee being restricted by an articulating surface on the bumper, which allows the femoral component to flex in the anterior posterior direction.

2. The knee prosthesis as claimed in claim 1 in which the axis of the hearing is inclined laterally relative to the axis of the femoral component so that it is able to line up with a mechanical axis of a lower limb.

3. The knee prosthesis as claimed in claim 2 in which the axis of the bearing is inclined laterally relative to the axis of the femoral component at an angle of about 5°.

4. The knee prosthesis as claimed in claim 1 in which the axis of the bearing is inclined posteriorly at an angle of about 20°.

5. The knee prosthesis as claimed in claim 1 in which the bearing has a domed inner end and a short circular cylindrical part extending from the domed inner end.

6. The knee prosthesis as claimed in claim 1 in which the bearing has a slot cooperating with a stem carrying the ball of the ball and socket joint to provide for bending of the prosthesis in use, corresponding to the angles of flexing of the prosthetic knee of from 0° to about 130°.

7. The knee prosthesis as claimed in claim 1 in which the ball of the hall and socket is carried, by a stem fitted into a cylindrical socket provided in the platform of the tibial component with the stem being held captive in the cylindrical socket by an offset transverse fastener having a smooth cylindrical section cooperating tangentially with a circumferential groove in the outer surface of the stem.

8. The knee prosthesis as claimed in claim 1 in which the tibial component has a tapered socket for receiving a tibial intramedullary stem in taper lock cooperation with each other.

9. The knee prosthesis as claimed in claim 8, in which medial and lateral fins stabilise the platform relative to the tapered socket.

10. The knee prosthesis as claimed in claim 1 in which the bumper has shaped surfaces cooperating with the condylar surfaces of the femoral component with the bumper being attached to the platform of the tibial component by inter-engaging dovetail formations at one end of a pair of parallel laterally spaced shoe formations on the under surface of the bumper and a pair of oppositely directed catches formed integral with the platform.

* * * * *